US006232296B1

(12) United States Patent
Henry

(10) Patent No.: US 6,232,296 B1
(45) Date of Patent: May 15, 2001

(54) INHIBITION OF COMPLEMENT ACTIVATION AND COMPLEMENT MODULATION BY USE OF MODIFIED OLIGONUCLEOTIDES

(75) Inventor: Scott Henry, Cardiff, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/409,816

(22) Filed: Sep. 30, 1999

(51) Int. Cl.$^7$ .............................. A61K 48/00; C12Q 1/68; C12P 19/34; C12N 15/85; C07H 21/04

(52) U.S. Cl. ................................ 514/44; 435/6; 435/91.1; 435/325; 435/363; 435/375; 536/23.1

(58) Field of Search ............................... 435/6, 91.1, 325, 435/363, 366, 375; 514/44; 536/23.1

(56) References Cited

FOREIGN PATENT DOCUMENTS

| WO 95/32719 | 5/1995 | (WO). |
| WO 95/32719 A1 * | 12/1995 | (WO). |
| WO 97/07354 | 5/1997 | (WO). |

OTHER PUBLICATIONS

Henry, S.P. et al., Effects of Intravenous Infusion of Phosphorothioate Oligonucleotides on Coagulation, Complement Activation and Hemodynamics, Nucleosides & Nucleotides 16(7–9), 1673–1676 (1997).*

Henry, S.P. et al., Activation of the Alternative Pathway of Complement by a Phosphorothioate Oligonucleotide: Potential Mechanism of Action, J. Pharmacol. Exp. Ther. 281 (2), 810–816 (1997).*

Merriam Webster's Collegiate Dictionary, Tenth Edition, at p. 541–542 (1996).*

Henry, Scott P., et al., "Activation of the Alternative Pathway of Complement by a Phosphorothioate Oligonucleotide: Potential Mechanism of Action", *The Journal of Pharmacology and Experimental Therapeutics* 1997 vol. 281, No. 2, 810–816.

* cited by examiner

Primary Examiner—John L. LeGuyader
Assistant Examiner—Mark L. Shibuya
(74) Attorney, Agent, or Firm—Licata & Tyrrell P.C.

(57) ABSTRACT

Oligomeric compounds are described wherein said compounds comprise modified oligonucleotides (P=S) which modulate complement activity. Methods and processes for the uses of such oligomeric compounds are also described. The oligomeric compounds may be used therapeutically to modulate complement activity in order to inhibit undesirable complement mediated events, such as for example, to treat inflammation, and/or to activate complement.

3 Claims, 5 Drawing Sheets

INHIBITION OF COMPLEMENT ACTIVATION AND COMPLEMENT MODULATION BY USE OF MODIFIED OLIGONUCLEOTIDES

FIELD OF THE INVENTION

This invention concerns methods for the inhibition and/or modulation of the complement mediated immune response using synthetic nucleic acid molecules. The nucleic acid molecules may be synthetic nucleic acid molecules, such as oligonucleotides, wherein at least one of the ester linkage moieties of the oligonucleotide is replaced with a thioate linkage, such as in for example phosphorothioates. The methods described herein are useful as therapies for treating abnormal and/or undesirable conditions which can arise as a result of complement activation. Further uses as diagnostics and research reagents are also included in the present invention.

BACKGROUND OF THE INVENTION

The complement system is an important means by which a host defends itself against infection. The complement cascade system is a component of the immune system that helps provide a natural immunity against invading microbes and is also an effector arm of antibody mediated humoral immunity. Complement is responsible for activating cells and other molecules involved in the inflammatory process as well as being directly related to the destruction of microbial invaders. The activation of complement involves a cascade of proteolytic reactions that lead to the release of inflammatory mediators and result in the assembly of the microbial membrane attack complexes which, in turn, lyse invading microbial cells. This cascade system has been characterized as containing at least thirty serum and membrane proteins that are activated by antibody-antigen complexes or by the invasion, in a host or experimentally in culture, by a microorganism, or other antigenic molecules. Complement proteins may be grouped into three general categories: activating components, receptors, and positive and negative regulators.

The complement cascade consists of two major branches, the classical and alternative pathways. Though these pathways are initiated differently, they converge at the step of complement protein C3 activation (see FIG. 5). The complement cascade can mediate undesirable cellular damage in inflammatory, immune or autoimmune (auto-antibody-mediated) conditions such as; myasthenia gravis, immune complex excess syndromes such as systemic lupus erythematosus, ischemia-reperfusion states, hyper-acute rejection of transplants, organ failure conditions such as adult respiratory distress syndrome, Alzheimer's disease and related neurodegenerative disorders, among others.

A series of regulatory proteins are involved in the control of the complement cascade. These proteins are considered part of the complement system and act to block endogenous complement activity at either initiation or the formation of the membrane attack complex. various therapeutic agents are being developed that block different steps in the complement cascade.

Complement is a group of serum proenzymes that are activated by antigen bound immunoglobulin or by membrane components on gram negative bacteria or fungi. The alternative pathway of the complement system is initialized by either the introduction of an endotoxin such as lipopolysaccharide [LPS], a component of the cell walls of gram negative bacteria or for instance by zymosan, a component of yeast cell walls, or by aggregated IgA.

The classical pathway of the complement system is initialized by Complement protein C1 binding to antigen bound IgG or IgM. Both pathways converge at the formation of C3 convertase at which point an amplification takes place that generates literally thousands of C3a and C3b fragments. C3b fragments can bind to complement protein complex C4b2a to form C4b2a C3b which is called C5 convertase and generates thousands of C5a and C5b fragments. C3b can also be used to regenerate C3 convertase which causes a greater amplification of complement protein split product C3a. Split products C3a and C5a interact with receptors on mast cells to cause them to release histamine. Histamine induces inflammation which is generally considered protective, but in conditions characterized by improper complement activation and/or regulation inflammation can lead to damaged tissue.

One approach to inhibit complement mediated effects is by depleting complement. Depleting complement involves reducing the proteins responsible for the regeneration of C3 or C5 convertase and thereby reducing the amount of C3a and C5a produced. In this way complement is depleted or "used up". One such method for depleting complement component C3 convertase involves allowing C3 convertase to form and then binding split product C3b in order to reduce the further amplification of C3 convertase formation which can lead to C5 convertase formation.

In another approach for inhibiting complement the pathway is inhibited before the formation of C3 convertase. Inhibition of the formation of C3 convertase limits the production of split products C3b and C3a and further limits the formation of C5 convertase. Using this approach complement activation is blocked rather than depleted.

Candinas et al., describe the activation and depletion of complement by using cobra venom factor in conjunction with a recombinant soluble complement receptor type 1 protein (sCR1), and the use of such molecules in treating hyperacute xenograft rejection. (Candinas, D. et al., *Transplantation* 1996 15;62(3):336–342) sCR1 is a recombinant protein that has been shown to inhibit both the classical and alternative pathways of complement and thereby limits the production of proinflammatory products such as the anaphylatoxins (complement proteins C3a, C4a and C5a). sCR1 has also been described by Moore, F D Jr., as the first protein useful to treat adverse clinical situations which are complement-dependent, and further describes potential uses for sCR1 to treat thermal injury, ARDS, septic shock, and ischaemia/reperfusion injury events such as myocardial infarction after thrombolytic therapy. (Moore, F D Jr., *Adv. Immunol* 1994 56:267–299) U.S. Pat. No. 5,856,297, Fearon et al., issued Jan. 5, 1999 claims pharmaceutical compositions comprising a CR1 protein in various modifications and describes CR1 and the recombinant forms of the protein as being useful in the diagnosis and treatment of disorders involving complement activity and inflammation.

Other proteins have been investigated for their usefulness in inhibiting or modulating complement. For instance, Human IgG has been used to balance complement activation in a pig-to-primate cardiac xenotransplantation hyperacute rejection study. The study determined that Human IgG caused a dose-dependent decrease in deposition of complement protein iC3b and a decrease in formation of C3 convertase. Furthermore, the infusion of IgG was found to prevent hyperacute rejection of porcine hearts transplanted into the primates. Magee J. C. et al., *J.Clin.Invest* 1995 96(5):2404–2412. U.S. Pat. No. 5,851,528, Ko et al., issued Dec. 22, 1998, U.S. Pat. No. 5,679,546, Ko et al., issued Oct. 21, 1997, and U.S. Pat. No. 5,627,264, Fodor et al., issued May 6, 1997, describe chimeric proteins useful in inhibiting complement activation and describe methods to treat adverse conditions related to complement mediated inflammation. Sims, et al., U.S. Pat. No. 5,550,508, issued Aug. 27, 1996, describes polypeptides which act to inhibit complement C5b-9 complex activity. The protein is an 18 kDA protein found on the surface of human erythrocytes and is described as being useful in treating immune disease states when administered in effective amounts.

Magee, J. C. et al., *J. Clin. Invest.* 1995 96(5):2404–12, investigated the use of immunoglobulin to prevent complement-mediated hyperacute rejection in swine-to-primate xenotransplantation. In the study human IgG was added to human serum and was found to cause a dose-dependent decrease in the deposition of iC3b, cytotoxicity, and heparin sulfate release when the serum was incubated with porcine endothelial cells. It appears as if the decrease was caused by a decrease in the formation of C3 convertase on the endothelial cells. Furthermore, infusion of purified human IgG into primates prevented hyperacute rejection of porcine hearts in a xenotransplantation. Magee et al., determined that such results support the use of IgG as a therapeutic agent in humoral-mediated disease conditions.

U.S. Pat. No. 4,374,831, Joseph et al., issued Feb. 22, 1983, U.S. Pat. No. 4,087,548, Lenhard et al., issued May 2, 1978, U.S. Pat. No. 4,021,545, Nair et al., issued May 3, 1977, and U.S. Pat. No. 3,998,957, Conrow et al., issued Dec. 21, 1976, all describe chemical molecules which are useful as inhibitors and/or modulators of complement. Josephe et al., describe Bis-($\beta$-D-glucopyranosyl-1-oxy)-arylene sulfate derivatives and methods for modulating complement in a warm blooded animal using pharmaceutical compounds comprising such molecules. Lenhard et al., describe complement inhibitory compounds such as C-substituted trisulfonic acids, acid ureides, and oxalyl amides and methods for inhibiting the complement system in a warm blooded animal by administering complement inhibitory amounts of the compounds comprising such molecules. Nair et al., claim methods for inhibiting the complement system in a warm blooded animal by using compositions comprising Inulin poly(H-sulfate). Conrow et al., describe 1,1'-[ureylenebis(sulfo-p-phenylene)]bis{sulfo-1H, 8H-indazolo{2,3,4-cde]benzotriazol-9-ium hydroxide}, bis (inner salts), and tetra salts as useful complement inhibitors.

In WO 95/32719 (1995), Galbraith describes the use of phosphorothioate oligonucleotides for depleting complement. The approach described involves administering, to a primate, an oligonucleotide 2 to 50 nucleotides in length containing at least one phosphorothioate internucleotide linkage, thereby stimulating vasodilation, and reducing complement activity by depleting complement.

Lin et al., WO 97/42317, describe oligonucleotides (aptamers) having phosphorothioate and/or substituted phosphonate linkages that are 37–61 base pairs in length which bind complement protein C3b and may be used diagnostically in vivo or in vitro to detect C3b in a biological sample. The aptamers may be used therapeutically to inhibit undesirable C3b-mediated complement events such as inflammation.

There has been and continues to be a long-felt need for methods for the inhibition and/or modulation of the complement mediated immune response using modified oligonucleotide compounds that might incorporate modifications for improving characteristics such as compound stability and cellular uptake. Such methods would be useful for therapeutically and prophylactically, as well as for diagnostic reagents and research reagents including reagents for the study of both cellular and in vitro events.

SUMMARY OF THE INVENTION

This invention relates to methods for modulating complement activation. These methods incorporate using modified oligonucleotides capable of inhibiting complement activation and/or initiating complement activation, depending on oligonucleotide concentration, and thereby provide a method for modulating complement. The methods are also useful therapeutically for the treatment of abnormal and/or undesirable conditions which can arise as a result of complement activation. Other uses for the methods presently described, such as for example as diagnostics and research reagents, are also included.

Thus in a first aspect, the present invention features methods for modulating complement activation by independently administering to tissue, cells, cell/tissue culture, a bodily fluid, or a biological sample, a modified oligonucleotide in two different concentrations. Preferably, the first administered concentration initiates complement activation and the second concentration inhibits complement activation, although it is within the scope of the invention to have the first administered concentration inhibit complement activation and the second administered concentration initiate complement activation. In an embodiment of the invention, the initiating concentration of modified oligonucleotide is no greater than 80 $\mu$g/ml, and more preferably between 50 $\mu$g/ml and 80 $\mu$g/ml, and the inhibitory concentration of modified oligonucleotide is at least 200 $\mu$g/ml, and more preferably between 250 $\mu$g/ml and 300 $\mu$g/ml.

Most preferably the inhibitory concentration is greater than the activating concentration. Within the scope of the invention are further concentrations determined through methods such as titration wherein concentration levels are determined based on the condition or extent to which complement modulation is desired.

In preferred embodiments the methods are performed in vitro or ex vivo and are preferably performed on a bodily fluid sample or a biological sample such as for example a mammalian blood or serum sample. More preferably the mammalian blood or serum sample is from a primate, and most preferably the sample is from a human. Within this embodiment the biological fluid sample includes samples of tissue or cells, wherein the sample also contains complement components.

In other embodiments the methods are performed in vivo in a mammal. Preferably the mammal is a primate and most preferably the primate is a human.

In an additional embodiment the present invention provides methods for treating a human subject determined to have an abnormal or undesirable condition associated with complement activation by administering a first and second concentration of an oligonucleotide compound which modulates complement activity. Preferably the compound is administered in a first initiating concentration and a second inhibitory concentration. The oligonucleotide preferably contains one or more phosphorothioate modifications. It is preferred that the modulating concentrations are similar to those discussed above for both the first and second administration.

In more preferred embodiments the methods for treating are performed ex vivo on a cell culture, tissue sample, bodily fluid or a biological sample taken from a human. Most preferably the methods are performed in vivo in a human subject having an abnormal or undesirable condition associated with complement activation as determined by a licensed physician.

In an additional aspect the methods described herein feature an oligonucleotide which contains at least one phosphorothioate (P=S) modification and which modulates complement activity by initiating complement activation at a first oligonucleotide concentration and inhibiting complement activation at a second oligonucleotide concentration. The inhibition and initiation concentrations of the modified oligonucleotide are independent and separate measurements and are not considered to be the total concentration of oligonucleotide in a sample or host. What is most preferred is that the first (initiating) concentration of the modified oligonucleotide be lower than the second (inhibiting) concentration of the same oligonucleotide.

It is preferred that the concentration of oligonucleotide required to initiate complement activation be less than or equal to 80 µg/ml, and more preferably the concentration required to initiate complement activation is between 50 µg/ml and 80 µg/ml. Within this same aspect of the invention, it is presently preferred that the concentration of oligonucleotide required to inhibit complement activation be at least 200 µg/ml; more preferably the concentration required to inhibit complement activation is between 250 µg/ml and 300 µg/ml. In regard to the first and second concentrations of oligonucleotide the preferred embodiments are not considered limiting.

Included in the invention, are methods for modulating complement activation in a cell culture, tissue or a bodily fluid by administering a modified oligonucleotide compound which inhibits complement activation and which contains at least one phosphorothioate modification and is conjugated to a complement activation inhibitory molecule. In preferred embodiments the methods are performed in vitro or ex vivo and are preferably performed on a bodily fluid sample, cell culture or a biological sample such as for example a mammalian blood or serum sample. More preferably the mammalian blood or serum sample is from a primate, and most preferably the sample is from a human. Within this embodiment the biological fluid sample includes samples of tissue or cells, wherein the sample also contains complement components.

Preferably, the modified oligonucleotide contains at least one phosphorothioate modification and is conjugated to a complement activation inhibitory molecule. More preferably the complement activation inhibitory molecule is a serum, vascular or cellular ligand, small complement binding molecule, or a complement specific ligand. Most preferably the complement activation inhibitory molecule binds complement Factor H. Preferably, the modified oligonucleotide to which the complement activation inhibitory molecule is bound is up to 60 oligonucleotides in length; in more preferred embodiments the modified oligonucleotide which inhibits complement activation is between 8 and 30 nucleotides in length. In an additional aspect, the invention features a modified oligonucleotide compound which inhibits complement activation.

In other embodiments the methods are performed in vivo in a mammal. Preferably the mammal is a primate and most preferably the primate is a human.

The term "independently administering" as used herein means providing one concentration (inhibitory or initiating) of modified oligonucleotide to the host and/or host cells at a time in order to modulate complement activity. The manner in which the modified oligonucleotide is administered may be selected from, but is not limited to: intravenous infusion, needle injection, topical, needle-free injection as in, for example, an injection using a device like the Medi-Jector™, and by aliquots using a pipette or similar device.

By use of term "culture" is meant the propagation of cells. Various culture methods exist and are included within the scope of the invention, methods such as, but not limited to, tissue culture methods, batch culture methods, enrichment culture methods, and ex vivo culture methods. In all culture methods the cells to be propagated should be in a nutritive environment which allows for continued cell growth, complement activation and/or inactivation. Tissue and cell culture methods are well understood in the art as these methods have been regularly practiced in various scientific fields for years. Such cultures may be propagated in natural serum or in artificial serum as described for example in U.S. Pat. No. 4,657,866 to Kumar, Sudhir. Inasmuch as a culture represents a group of cells being observed for effects relating to complement activation or inhibition, included within the scope of the invention are cultures of cells on or in a host, such as a mass of burned tissue or cells, or a tumor growth, which must remain on or in the host to be propagated.

By the phrase "monitoring complement activity" is meant measuring products of the proteolytic complement cascade. Such products to be measured include, but are not limited to, complement proteins: C5a, C3a, and C4a. Methods for measuring products of the complement cascade are disclosed hereinbelow and can include antibody specific labeling of complement proteins C5A, C3a and C4a and performing ELISA assays to determine the relative concentration of the split products formed. In general monitoring of complement activity is performed on a biological sample that has been taken from a subject, patient or host, such as for example a serum or blood sample or other bodily fluid.

Further aspects of the invention are described within the description of the preferred embodiments. The summary of the invention described above is not limiting and other features and advantages of the invention will be apparent from the following detailed description of the invention and from the claims.

BRIEF DESCRIPTION OF THE DRAWINGS

The drawings will herein briefly be described.

DETAILED DESCRIPTION OF PREFERRED EMBODIMENTS

Figure 1:
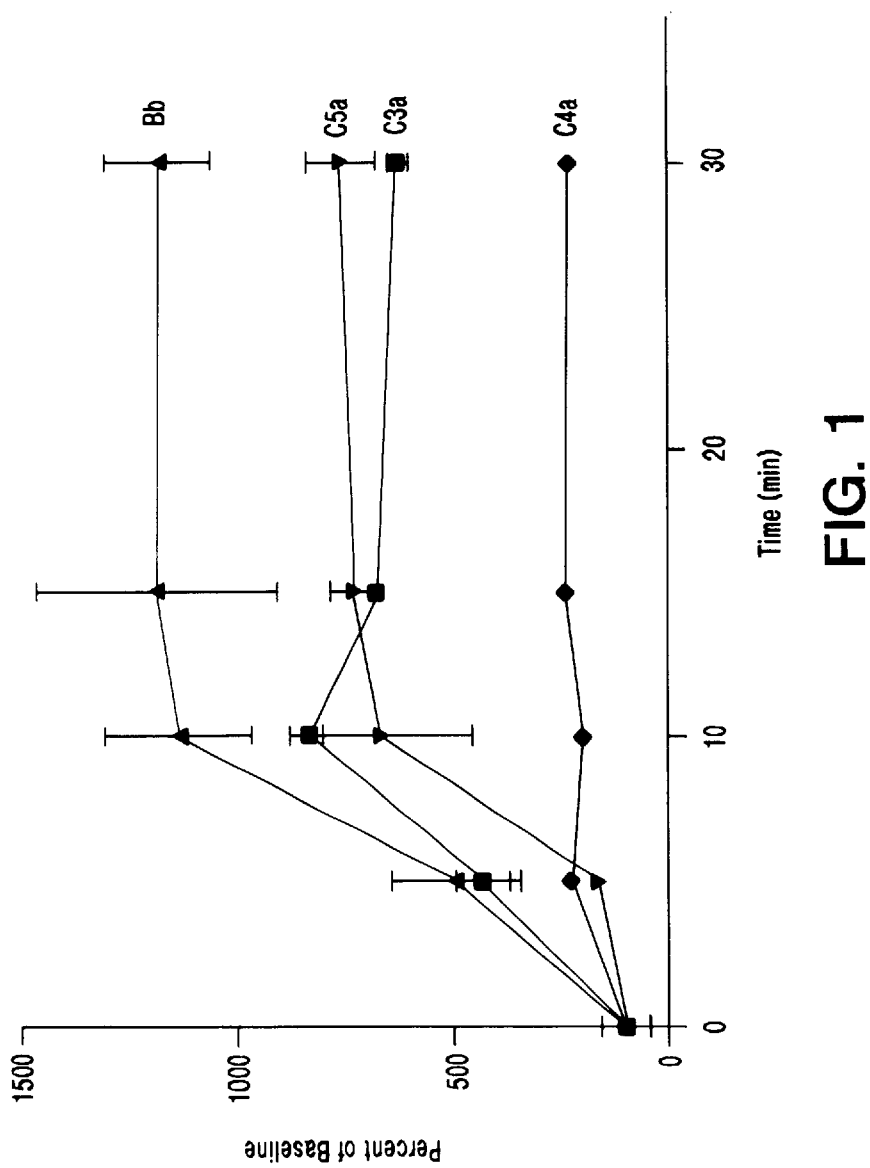
FIG. 1 is a line graph which shows the activation of complement in monkey serum by the addition of 100 µg/ml of a phosphorothioate oligonucleotide (ISIS 2302; SEQ ID NO:1) of the invention as measured by the amounts of complement components compared to baseline levels.
Figure 2:
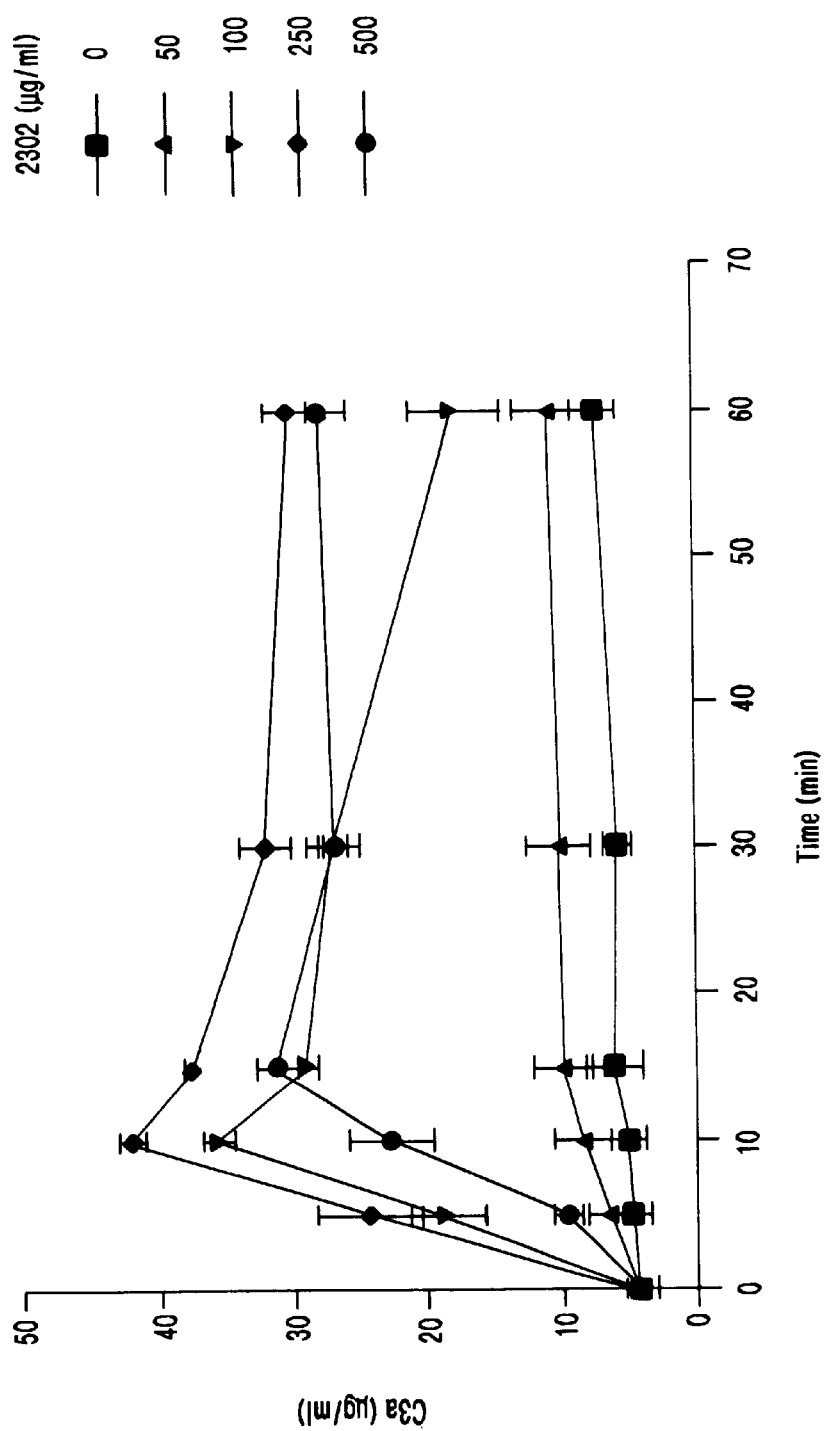
FIG. 2 is a line graph which shows the measurement of complement component C3a to determine complement activation over a range of added concentrations of a phosphorothioate oligonucleotide of the present invention (ISIS 2302; SEQ ID NO:1)
Figure 3:
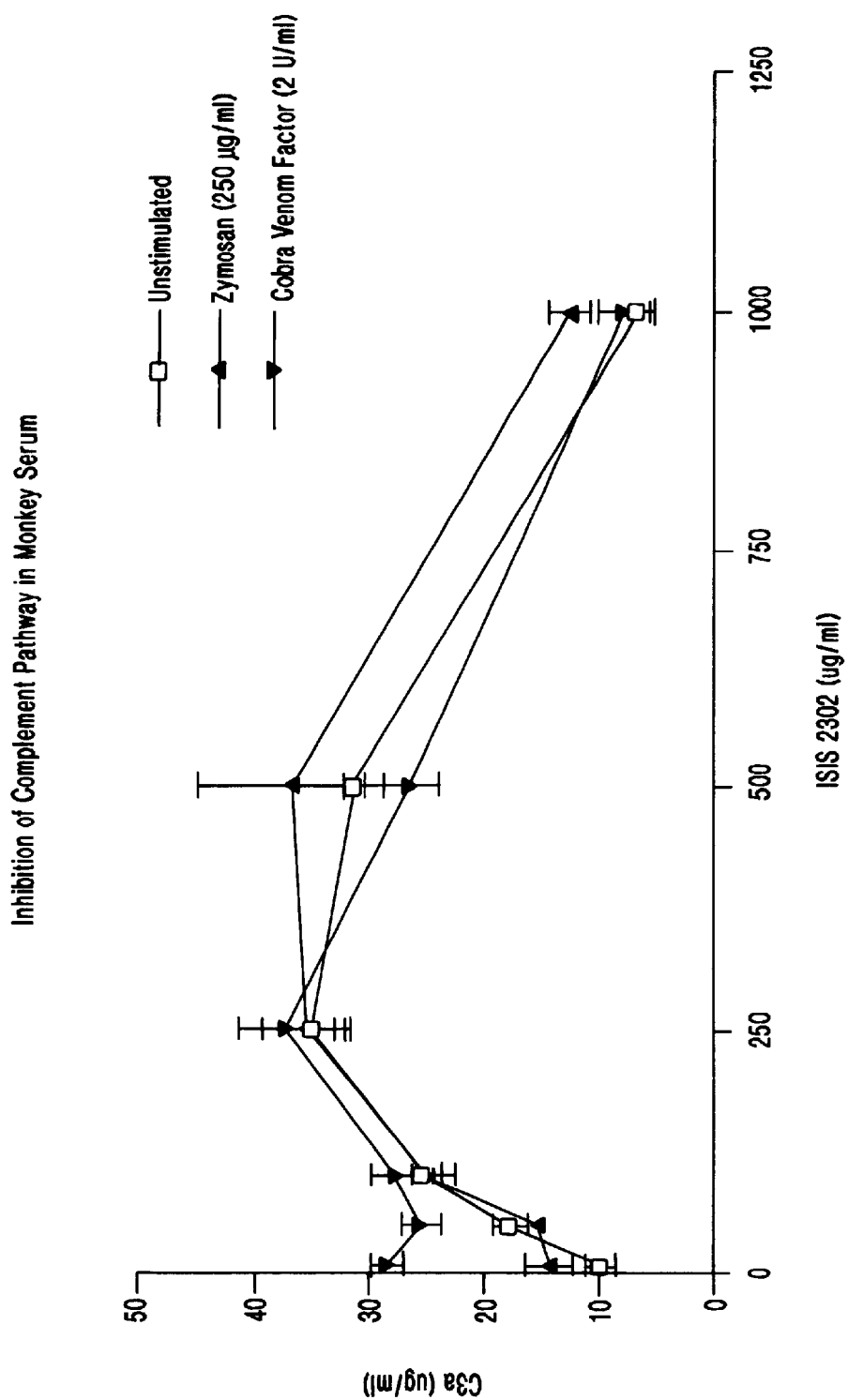
FIG. 3 is a line graph which shows the inhibition of complement activation as measured by the amount of complement component C3a in monkey serum after stimulating complement activation with cobra venom factor or zymosan. Inhibition is measured over a concentration range of added phosphorothioate oligonucleotide (ISIS 2302; SEQ ID NO:1) as described herein.
Figure 4:
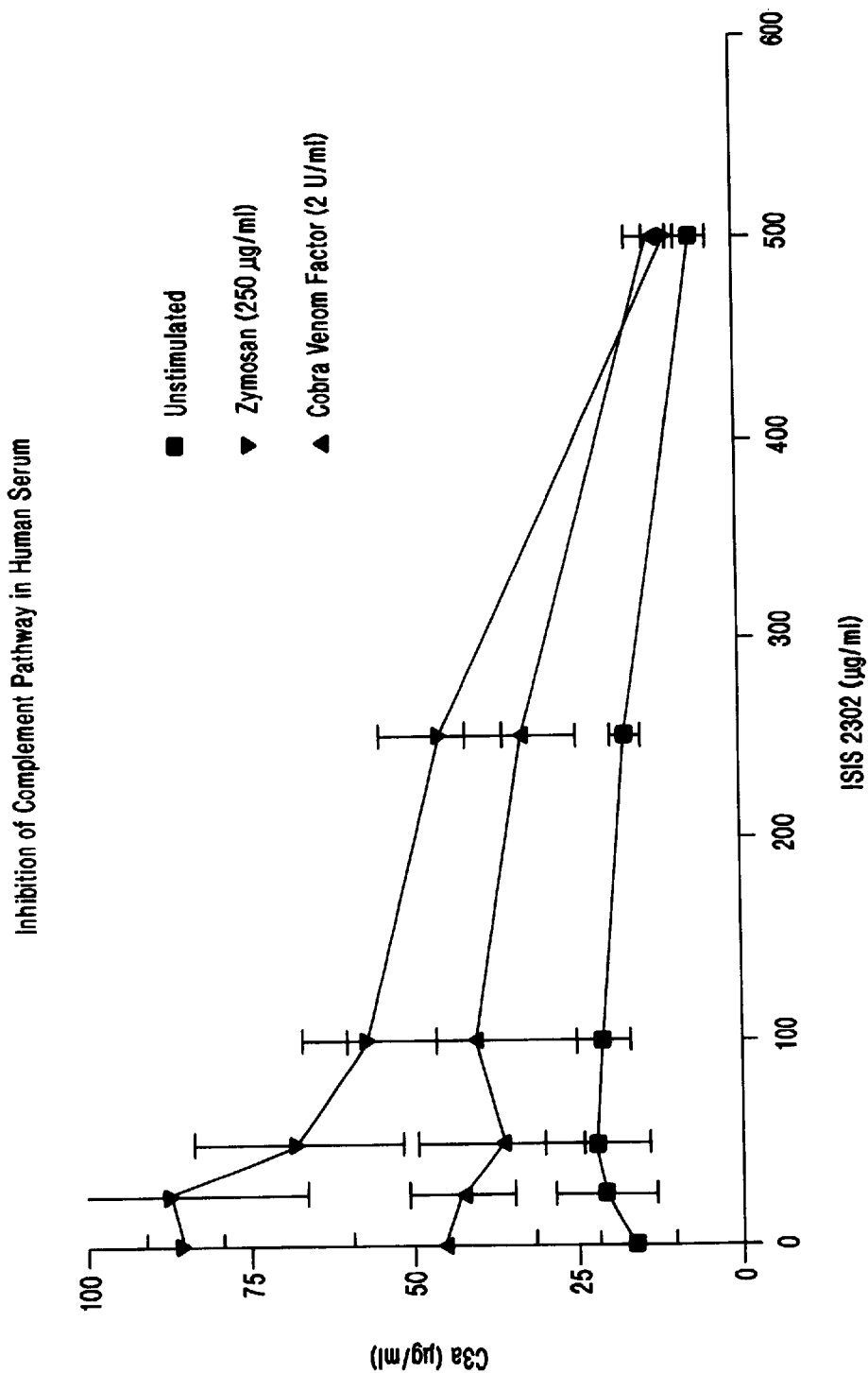
FIG. 4 is a line graph which shows the inhibition of complement activation as measured by the amount of complement component C3a in human serum after stimulating complement activation with cobra venom factor or zymosan. Inhibition is measured over a concentration range of added phosphorothioate oligonucleotide (ISIS 2302; SEQ ID NO:1) as described herein.
Figure 5:
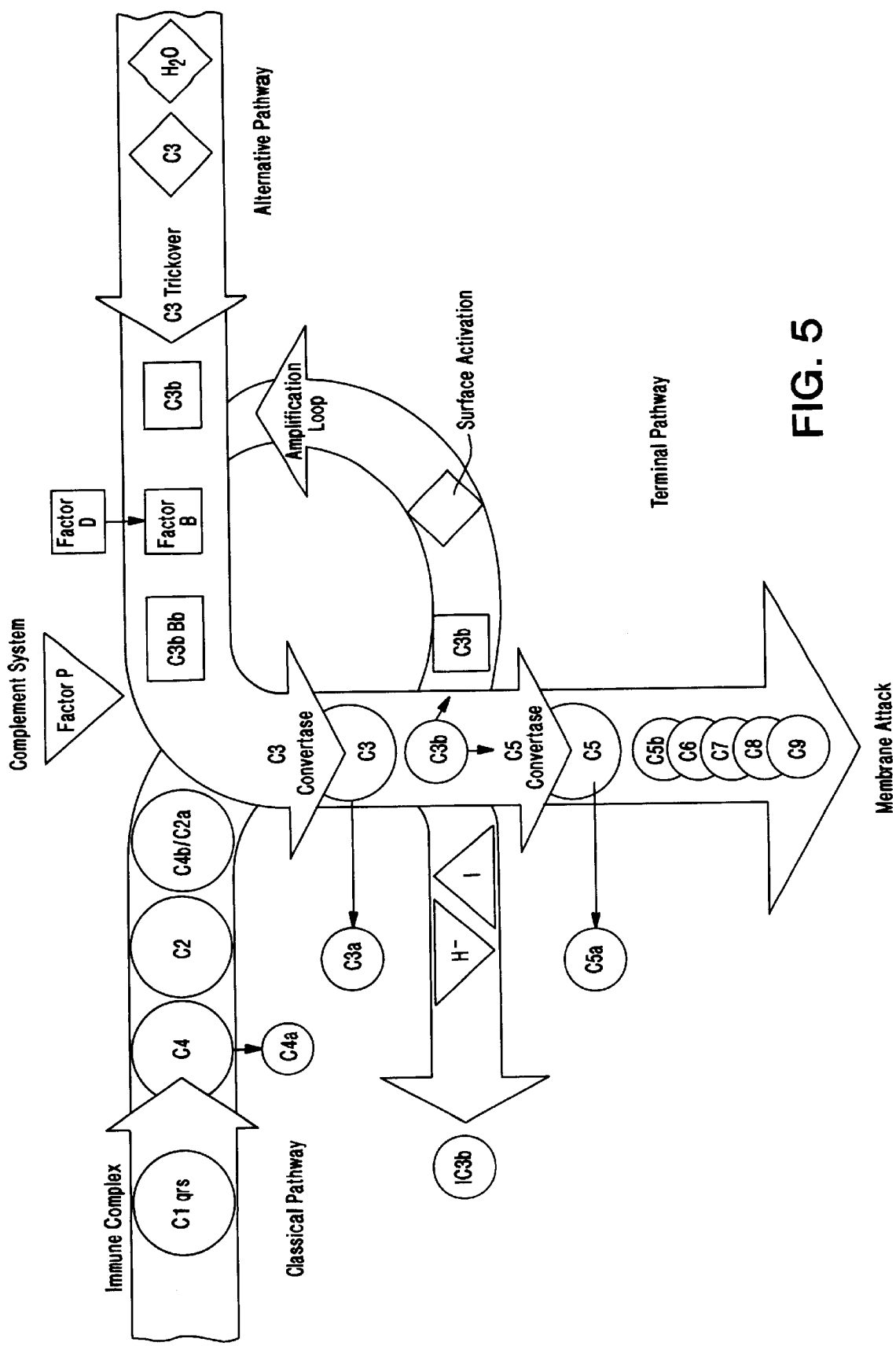
FIG. 5 shows a schematic representation of the complement system.

Complement comprises a proteolytic cascade of serum and membrane proteins which are part of the immune system and are responsible for protecting hosts against foreign pathogens.

The complement system has powerful cytolytic activity which can damage an individual's own cells and should therefore be a target for modulation in order to reduce injury in various autoimmune events. In most cases individuals possess proteins which can control the extent of complement activation in serum or on the surfaces of "self" cells. Most of the proteins which inhibit complement activation in serum serve to limit the generation of complement fragments such as C4b and C3b. Proteins such as C1-inhibitor, C4-binding protein, Factor H, and Factor I serves as normal inhibitors of complement in "normal" individuals. In an non-limiting example, C1 inhibitor is not present due to a genetic deletion or point mutations that produce an inactive form and results in hereditary angioedema of which there is also an acquired form usually due to auto-antibody to C1 INH. In such an abnormal condition such as angioedema as in others there is a need to help modulate complement in order to reduce the damage that can occur.

As described above, various methods have been investigated to inhibit complement activation. Wuillemin et al., *J. Immunol* 15;159(4):1953–60, (1997), describes the use of glycosaminoglycans, such as heparin, to inhibit the interaction of complement component C1q with other complement activators and the assembly of the classical and alternative pathway C3 convertases. Naturally occurring glycosaminoglycans such as dextran sulfates, heparin, N-acetylheparin, heparan sulfate, dermatan sulfate, and chondroitin sulfates A and C were studied to determine their effectiveness at inhibiting the deposition of C4 and C3 on immobilized aggregated human IgG and to reduce fluid phase formation of C4b/c and C3b/c. In the study it was concluded that glycosaminoglycans such as the low molecular weight dextran sulfate (m.w. 5000) may serve as candidates for pharmacological manipulation of complement activation via potentiation of C1 inhibitor.

We have found that activation of the alternative pathway of complement occurs following the intravenous infusion of modified oligodeoxynucleotides (P=S oligo). By using monkey serum and whole blood we determined that modified oligonucleotides cause an increase in complement products Bb, C3a, and C5a. The concentration that was found to activate complement in these experimental systems was found to be up to roughly 50 $\mu$g/ml. By using the same modified oligonucleotide (ISIS 2302; SEQ ID NO:1) it was determined that at concentrations of roughly 250 $\mu$g/ml and greater complement activation was inhibited in both the classical and alternative pathways as indicated by a reduction in complement components Bb, C3a, and C5a.

The present invention provides methods for modulating complement activity using modified oligonucleotides. The invention provides methods for using modified oligonucleotides which involve administering the oligonucleotides at one concentration to initiate complement activation and at another concentration to inhibit complement activation. The oligonucleotides of the present invention are modified to have improved pharmacokinetic properties. The methods described herein are useful as therapeutics for the treatment, prevention or diagnosis of abnormal and/or undesirable conditions which can arise as a result of complement mediated inflammatory effects.

By "abnormal and/or undesirable conditions" is meant any conditions that have an inflammatory, immune or autoimmune component associated with the activation of the complement cascade. An abnormal and/or undesirable condition can be, but is not limited to: myasthenia gravis, immune complex excess syndromes such as systemic lupus, erythematosus, ischemia-reperfusion states, angioedema, hyper-acute rejection of transplants, organ failure conditions such as adult respiratory distress syndrome, Alzheimer's disease and related neurodegenerative disorders. Such conditions are generally determined by registered physicians.

Other envisioned treatments are for conditions in which a host is invaded by a foreign body which avoids the complement system and which may be targeted by an oligonucleotide according to the present invention in order to activate the complement system and eliminate the invading molecule.

Modifications of Oligonucleotides

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such "modified" or substituted oligonucleotides are often preferred over native forms because of desirable properties such as, for example, enhanced cellular uptake, enhanced binding to target, increased stability in the presence of nucleases and an increase in bioavailability. In the present invention, oligonucleotides having at least one phosporothioate modification are preferred.

Within the concepts of "oligonucleotides" and "modified" oligonucleotides, the present invention also includes compositions employing oligonucleotide compounds which are chimeric compounds. "Chimeric" oligonucleotide compounds or "chimeras," in the context of this invention, are nucleic acid compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or consist of an oligomeric sequence known to modify complement activation. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate oligodeoxynucleotides hybridizing to the same target region. Cleavage of the RNA target can be routinely detected by gel electrophoresis and, if necessary, associated nucleic acid hybridization techniques known in the art. RNase H-mediated target cleavage is distinct from the use of ribozymes to cleave nucleic acids.

By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for, or stability when duplexed with, the target RNA molecule but are unable to support nuclease activity (e.g., 2'-fluoro- or 2'-methoxyethoxy-substituted). Other chimeras include "hemimers," that is, oligonucleotides in which the 5' portion of the oligonucleotide serves as a substrate for, e.g., RNase H, whereas the 3' portion is modified in such a fashion so as to have greater affinity for, or stability when duplexed with, the target RNA molecule but is unable to support nuclease activity (e.g., 2'-fluoro- or 2'-methoxyethoxy- substituted), or vice-versa.

A number of chemical modifications to oligonucleotides that confer greater oligonucleotide:RNA duplex stability have been described by Freier et al. (*Nucl. Acids Res.*, 1997, 25, 4429). Such modifications are preferred for the RNase H-refractory portions of chimeric oligonucleotides and may generally be used to enhance the affinity of an antisense compound for a target RNA. In this way, in a preferred embodiment, a chimeric molecule comprised of a modified oligonucleotide which modulates complement and an antisense portion may be administered in order to target a specific RNA molecule and modulate complement mediated adverse effects.

Chimeric modified oligonucleotide compounds of the invention may be formed as composite structures of two or more oligonucleotides, modified oligonucleotides, oligonucleosides and/or oligonucleotide mimetics as described above, ligand-oligonucleotide constructs, or complement protein-oligonucleotide constructs as described herein. Some of these compounds have also been referred to in the art as hybrids or gapmers. Representative United States patents that teach the preparation of some of these hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and U.S. Pat. No. 5,700,922, certain of which are commonly owned, and each of which is herein incorporated by reference, and commonly owned and allowed U.S. patent application Ser. No. 08/465,880, filed on Jun. 6, 1995, now U.S. Pat. No. 5,955,589 also herein incorporated by reference.

Modifications to an oligonucleotide molecule can alter the concentration of the molecule required to elicit the effect for which the molecule is designed. Non limiting examples include varying the amount of phosphorothioate linkages in the oligonucleotide or altering the oligonucleotide base composition and chemistry such as in the preparation of CpG oligodeoxynucleotides as described by Krieg et al., Nature 1995 374:546–549, Weiner et al., Proc. Natl. Acad. Sci. USA 1997 94:10833–10837, Liu, HM et al., Blood 1998 15;92(10):3730–3736, Boggs, RT et al., Antisense Nucleic Acid Drug Dev 1997 7(5):461–471, and Kline et al., J.Immunol 1998 15;160(6):2555–2559, which are all hereby incorporated herein in their entirety including any figures and drawings.

The present invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521,302).

Oligonucleotides may contain modifications of the backbone sugar and/or nucleobase, singly or in combination. Specific examples of some preferred backbone modified oligonucleotides envisioned for this invention include those containing phosphorothioates (P=S oligonucleotides), phosphotriesters, methyl phosphonates, short chain alkyl or cycloalkyl intersugar linkages or short chain heteroatomic or heterocyclic intersugar linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and borano-phosphates having normal 3'-5' linkages, 2'-5' linked analogs of these, and those having inverted polarity wherein the adjacent pairs of nucleoside units are linked 3'-5' to 5'-3'or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497–1500.

Other preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O—(2-methoxyethyl) or 2'-MOE) (Martin et al., Helv. Chim. Acta, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples hereinbelow.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858–859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289–302, Crooke, S. T. and Lebleu, B. , ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553–6556), cholic acid (Manoharan et al., Bioorg. Med. Chem. Let., 1994, 4, 1053–1060), a thioether, e.g., hexyl-S-tritylthiol (Manoharan et al., Ann. N.Y. Acad. Sci., 1992, 660, 306–309; Manoharan et al., Bioorg. Med. Chem. Let., 1993, 3, 2765–2770), a thiocholesterol (Oberhauser et al., Nucl. Acids Res., 1992, 20, 533–538), an aliphatic chain, e.g., dodecandiol or undecyl residues (Saison-Behmoaras et al., EMBO J., 1991, 10, 1111–1118; Kabanov et al., FEBS Lett., 1990, 259, 327–330; Svinarchuk et al., Biochimie, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651–3654; Shea et al., Nucl. Acids Res., 1990, 18, 3777–3783), a polyamine or a polyethylene glycol chain (Manoharan et al., Nucleosides & Nucleotides, 1995, 14, 969–973), or adamantane acetic acid (Manoharan et al., Tetrahedron Lett., 1995, 36, 3651–3654), a palmityl moiety (Mishra et al., Biochim. Biophys. Acta, 1995, 1264, 229–237), or an octadecylamine or hexylamino-carbonyl-oxycholesterol moiety (Crooke et al., J. Pharmacol. Exp. Ther., 1996, 277, 923–937.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide.

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The $N^6$ position of a purine nucleobase may also be utilized to link a lipophilic moiety to an oligonucleotide of the invention (Gebeyehu, G., et al., *Nucleic Acids Res.,* 1987, 15, 4513). Such lipophilic moieties include but are not limited to a cholesteryl moiety (Letsinger et al., *Proc. Natl. Acad. Sci. USA,* 1989, 86, 6553), cholic acid (Manoharan et al., *Bioorg. Med. Chem. Let.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), or adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylamino-carbonyl-oxycholesterol moiety (Crooke et al., *J. Pharmacol. Exp. Ther.,* 1996, 277, 923). Oligonucleotides comprising lipophilic moieties, and methods for preparing such oligonucleotides, as disclosed in U.S. Pat. Nos. 5,138,045, 5,218,105 and 5,459,255, the contents of which are hereby incorporated by reference in their entirety.

In other preferred embodiments the compound may be a ligand conjugated oligomeric compound having improved pharmacokinetic properties. Such oligomeric compounds are prepared having covalently attached ligands or proteins that bind reversibly to or interact with one or more serum, vascular or cellular proteins. This reversible binding is expected to decrease urinary excretion, increase serum half life and greatly increase the distribution of oligomeric compounds thus conjugated. In the case of binding a complement protein, such as for example complement Factor H or a ligand thereof, in the context of the present invention the binding is to further inhibit complement activity. The binding of particular drugs to plasma protein has been previously shown to enhance the disposition and efficacy of drugs (Herve et al., *Clin. Pharmacokinet.,* 1994, 26:44).

An oligomeric agent should be able to overcome inherent factors such as rapid degradation in serum, short half life in serum and rapid filtration by the kidneys with subsequent excretion in the urine. Oligonucleotides that overcome these inherent factors have increased serum half lives, distribution, cellular uptake and hence improved efficacy. These enhanced pharmacokinetic parameters have been shown for selected drug molecules that bind plasma proteins (Olson and Christ, *Annual Reports in Medicinal Chemistry,* 1996, 31:327). Two proteins that have been studied more than most are human serum albumin (HSA) and α-1-acid glycoprotein. HSA binds a variety of endogenous and exogenous ligands with association constants typically in the range of $10^4$ to $10^6$ $M^{-1}$. Association constants for ligands with α-1-acid glycoprotein are similar to those for HSA.

At least for therapeutic purposes, oligonucleotides should have a degree of stability in serum to allow distribution and cellular uptake. The prolonged maintenance of therapeutic levels of oligomeric agents in serum will have a significant effect on the distribution and cellular uptake and unlike conjugate groups that target specific cell receptors the increased serum stability will affect all cells. Numerous efforts have focused on increasing the cellular uptake of oligonucleotides including increasing the membrane permeability via conjugates and cellular delivery of oligonucleotides.

Many drugs reversibly bind to plasma proteins. A representative list, which is not meant to be inclusive, includes: aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, benzothiadiazides, chlorothiazide, diazepines (such as for example fludiazepam and diazepam) indomethacin, barbiturates (such as for example quinalbarbitone), cephalosporins, sulfa drugs, antidiabetics (such as for example tolbutamide), antibacterials (such as for example a group of quinolones; nalidixic acid and cinoxacin) and several antibiotics. Serum albumin is the most important protein among all plasma proteins for drug binding, although binding to other proteins (for example, macroglobulin $G_2$, immunoglobulins, lipoproteins, alpha-1-acid glycoprotein, thrombin) is also important.

Ligands that bind serum, vascular or cellular proteins may be attached via an optional linking moiety to one or more sites on an oligonucleotide of the invention. These sites include one or more of, but are not limited to, the 2' position, 3'-position, 5'-position, the internucleotide linkage, and a nucleobase atom of any nucleotide residue. The attachment of ligands to such structures can be performed, according to some preferred embodiments of the invention, using a linking group, or without the use of such a linking group. Preferred linking groups of the invention include, but are not limited to, 6-aminoalkoxy linkers, 6-aminoalkylamino linkers, cysteamine, heterobifunctional linkers, homobifunctional linkers, and a universal linker (derived from 3-dimethoxytrityloxy-2-aminopropanol). A particularly preferred linking group for the synthesis of ligand conjugated oligonucleotides of the invention is a 6-aminohexyloxy group. A variety of heterobifunctional and homobifunctional linking moieties are available from Pierce Co. (Rockford, Ill.). Such heterobifunctional and homobifunctional linking moieties are particularly useful in conjunction with the 6-aminoalkoxy and 6-aminoalkylamino moieties to form extended linkers useful for linking ligands to a nucleoside. Further useful linking groups that are commercially available are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, while the 3'-Amino-Modifier is also available from Clontech Laboratories Inc. (Palo Alto, Calif.). In addition, a nucleotide analog bearing a linking group pre-attached to the nucleoside is commercially available from Glen Research Corporation under the tradename "Amino-Modifier-dT." This nucleoside-linking group reagent, a uridine derivative having an [N(7-trifluoroacetylaminoheptyl) 3-acrylamido] substituent group at the 5 position of the pyrimidine ring, is synthesized as per the procedure of Jablonski et al. (*Nucleic Acid Research,* 1986, 14:6115). The present invention also includes as nucleoside analogs adenine nucleosides functionalized to include a linker on the N6 purine amino group, guanine nucleosides functionalized to include a linker at the exocyclic N2 purine amino group, and cytosine nucleosides functionalized to include a linker on either the N4 pyrimidine amino group or the 5 pyrimidine position. Such nucleoside analogs are incorporated into oligonucleotides with a ligand attached to the linker either pre- or post-oligomerization.

In a preferred embodiment of the present invention ligand molecules are selected for conjugation to oligonucleotides on the basis of their affinity for one or more complement proteins. These proteins may be serum, vascular or cellular proteins. Serum proteins are proteins that are present in the fluid portion of the blood, obtained after coagulation and removal of the fibrin clot and blood cells, as distinguished from the plasma in circulating blood. Vascular proteins are proteins that are present in portions of the vascular system relating to or containing blood vessels. Cellular proteins are membrane proteins which have at least a portion of the protein extending extracellularly and assisting in the process of endocytosis.

Many ligands having an affinity for proteins are well documented in the literature and are amenable to use in the present invention. A preferred group of ligands are small molecules including drug moieties. According to the present invention, drug moieties include, but are not limited to, warfarin and coumarins including substituted coumarins, isocoumarin derivatives, 7-anilinocoumarin-4-acetic acid, profens including ibuprofen, enantiomers of ibuprofen (r-ibuprofen and s,-ibuprofen), ibuprofen analogs, ketoprofen, carprofen, etodolac, suprofen, indoprofen, fenbufen, arylpropionic acids, arylalkanoic acids, 2-aryl-2-fluoropropionic acids, glibenclamide, acetohexamide, arylalkanoic acids, tolbutamide, gliclazide, metformin, curcumin, digitoxin, digoxin, diazepam, benzothiadiazides, chlorothiazide, diazepines, benzodiazepines, naproxen, phenyl butazone, oxyphenbutazone, dansyl amide, dansylsarcosine, 2,3,5-triiodobenzoic acid, palmitic acid, aspirin, salicylates, substituted salicylates, penicillin, flurbiprofen, pirprofin, oxaprozin, flufenamic acid, deoxycholic acid, glycyrrhizin, azathioprine, butibufen, ibufenac, 5-fluoro-1-typtaphan, 5-fluoro-salicylic, acidazapropanazone, mefenamic acid, indomethacin, flufenamic acid, bilirubin, ibuprofen, lysine complexes, diphenyl hydantoin, valproic acid, tolmetin, barbiturates (such as, for example, quinalbarbitone), cephalosporins, sulfa drugs, antidiabetics (such as, for example, tolbutamide), antibacterials (such as, for example, quinolones, nalidixic acid and cinoxacin) and several antibiotics.

In one embodiment of the present invention the drug moiety bears a carboxylic acid group. In another embodiment of the present invention the drug moiety is a propionic acid derivative.

In one preferred embodiment of the invention the protein for binding a ligand conjugated oligomeric compound is a serum protein. It is preferred that the serum protein bound by a conjugated oligomeric compound is an immunoglobulin (an antibody). Preferred immunoglobulins are immunoglobulin G and immunoglobulin M. Immunoglobulins are known to appear in blood serum and tissues of vertebrate animals. A more preferred protein for binding to a ligand conjugated oligomer is albumin.

In another embodiment of the invention the serum protein for binding by a conjugated oligomeric compound is a lipoprotein. Lipoproteins are blood proteins having molecular weights generally above 20,000 that carry lipids and are recognized by specific cell surface receptors. The association with lipoproteins in the serum will initially increase pharmacokinetic parameters such as half life and distribution. A secondary consideration is the ability of lipoproteins to enhance cellular uptake via receptor-mediated endocytosis.

In yet another embodiment the serum protein for binding by a ligand conjugated oligomeric compound is α-2-macroglobulin. In yet a further embodiment the serum protein targeted by a ligand conjugated oligomeric compound is α-1-glycoprotein.

As used herein, the term "protected" means that the indicated moiety has a protecting group appended thereon. In some preferred embodiments of the invention compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron*, 1992, 48:2223–2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y., 1991, each of which is hereby incorporated by reference in its entirety.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2, 6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p.1) and various substituted sulfonylethyl carbamates exemplified by the Nsc group (Samukov et al., *Tetrahedron Lett*, 1994, 35:7821; Verhart and Tesser, *Rec. Trav. Chim. Pays-Bas*, 1987, 107:621).

Additional amino-protecting groups include, but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl. Equivalents of these aminoprotecting groups are also encompassed by the compounds and methods of the present invention.

In a preferred embodiment of the present invention oligonucleotides are provided including a number of linked nucleosides wherein at least one of the nucleosides is a 2'-functionalized nucleoside having a ligand molecule linked to the 2'-position of the nucleoside; a heterocyclic base functionalized nucleoside having a ligand molecule linked to the heterocyclic base of the nucleoside, a 5' terminal nucleoside having a ligand molecule linked to the 5'-position of the nucleoside, a 3' terminal nucleoside having a ligand molecule linked to the 3'-position of the nucleoside, or an inter-strand nucleoside having a ligand molecule linked to an inter-stand linkage linking said inter-strand nucleoside to an adjacent nucleoside.

Ligand conjugated oligonucleotides may be synthesized by the use of an oligonucleotide that bears a pendant reactive functionality such as that derived from the attachment of a linking molecule onto the oligonucleotide. This reactive oligonucleotide may be reacted directly with commercially available ligands, ligands that are synthesized bearing a variety of protecting groups, or ligands that have a linking moiety attached thereto. The methods of the present invention facilitate the synthesis of ligand conjugated oligonucleotides by the use of, in some preferred embodiments, nucleoside monomers that have been appropriately conjugated with ligands and that may further be attached to a solid support material. Such ligand-nucleoside conjugates optionally attached to a solid support material are prepared according to some preferred embodiments of the methods of the present invention via reaction of a selected serum binding ligand with a linking moiety located on a 2', 3', or 5' position of a nucleoside or oligonucleotide.

The above described conjugation of ligands to oligomeric compounds has been shown to increase the concentration of such compounds in serum. According to such methods, a drug moiety that is known to bind to a serum protein is selected and conjugated to an oligonucleotide, thus forming a conjugated oligonucleotide. This conjugated oligonucleotide is then added to the serum.

Conjugation of a ligand also provides a way to increase the capacity of serum for an oligonucleotide. According to such methods, a drug moiety that is known to bind to a serum protein is selected and conjugated to an oligonucleotide, thus forming a conjugated oligonucleotide. This conjugated oligonucleotide is then added to the serum.

Ligand conjugation can also increase the binding of an oligonucleotide to a portion of the vascular system. According to such methods, a drug moiety that is known to bind to a vascular protein is selected. The vascular protein selected is a protein which resides, in part, in the circulating serum and, in part, in the non-circulating portion of the vascular system. This drug moiety is conjugated to an oligonucleotide to form a conjugated oligonucleotide, which is then added to the vascular system.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., Helv. Chim. Acta, 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other conjugated oligonucleotides.

Complement Modulation

The modified oligonucleotide compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids.

"Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.*, 1977, 66:1, which is incorporated herein by reference in its entirety).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE ((S-acetyl-2-thioethyl) phosphate) derivatives according to the methods disclosed in WO 93/24510 to Gosselin et al., published Dec. 9, 1993, which is incorporated herein by reference in its entirety.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems*, 1991, 8:91–192; Muranishi, *Critical Reviews in Therapeutic Drug Carrier Systems*, 1990, 7:1). One or more penetration enhancers from one or more of these broad categories may be included.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech., 1995, 6, 698). Liposomal modified oligonucleotide compositions are prepared according to the disclosure of co-pending U.S. patent application Ser. No. 08/961,469 to Hardee et al., filed Oct. 31, 1997, U.S. Pat. No. 6,083,923, incorporated herein by reference in its entirety.

The pharmaceutical compositions of the present invention may be administered in a number of ways depending upon whether local or systemic treatment is desired and upon the area to be treated. Administration may be topical (including ophthalmic, vaginal, rectal, intranasal, epidermal and transdermal), oral or parenteral, or by aliquots using a pipette or the like. Parenteral administration includes intravenous drip, injection or infusion, subcutaneous, intraperitoneal or intramuscular injection, pulmonary administration, e.g., by inhalation or insufflation, or intracranial, e.g., intrathecal or intraventricular, administration. Injection includes both needle injection and needle-free injection as in, for example, an injection using a device like the Medi-Jector™. For oral administration, it has been found that oligonucleotides with at least one 2'-substituted ribonucleotide are particularly useful because of their absorption and distribution characteristics. U.S. Pat. No. 5,591,721 issued to Agrawal et al. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

By "ex vivo" is meant removing a sample of blood, serum and/or bone marrow from a subject in need of complement modulation, treating the sample with the modified oligonucleotide described herein, and returning the sample to the subject.

Thus, in the context of this invention, by "therapeutically effective amount" is meant the amount of the compound which is required to have a therapeutic effect on the treated mammal. This amount, which will be apparent to the skilled artisan, will depend upon the type of mammal, the age and weight of the mammal, the type of disease to be treated, perhaps even the gender of the mammal, and other factors which are routinely taken into consideration when treating a mammal with a disease. A therapeutic effect is assessed in the mammal by measuring the effect of the compound on the disease state in the animal. For example, if the disease to be treated is an ischaemia-reperfusion event, a reduction in tissue damage is an indication that the administered dose has a therapeutic effect. In an example of a chimeric oligonucleotide usage, if the disease to be treated is psoriasis, a reduction or ablation of the skin plaque and a reduced activation of complement occurs this would also be an indication that the administered dose has a therapeutic effect. Similarly, in mammals being treated for cancer, therapeutic effects are assessed by measuring both the amount of complement activation and the rate of growth or the size of the tumor, or by measuring the production of compounds such as cytokines, production of which is an indication of the progress or regression of the tumor.

The following examples illustrate the present invention and are not intended to limit the same.

EXAMPLES

Example 1

Nucleoside Phosphoramidites for Oligonucleotide Synthesis

Deoxy and 2'-alkoxy Amidites

2'-Deoxy and 2'-methoxy beta-cyanoethyldiisopropyl phosphoramidites are purchased from commercial sources (e.g. Chemgenes, Needham Mass. or Glen Research, Inc. Sterling Va.).

Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides is utilized, except the wait step after pulse delivery of tetrazole and base is increased to 360 seconds.

Oligonucleotides containing 5-methyl-2'-deoxycytidine (5-Me-C) nucleotides are synthesized according to published methods [Sanghvi, et. al., Nucleic Acids Research, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides may be synthesized as described previously [Kawasaki, et. al., J. Med. Chem., 1993, 36, 831–841] and U.S. Pat. No. 5,670,633, herein incorporated by reference. Briefly, the protected nucleoside N6-benzoyl-2'-deoxy-2'-fluoroadenosine is synthesized utilizing commercially available 9-beta-D-arabin ofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine is selectively protected in moderate yield as the 3',5'-ditetrahydropyranyl (THP) intermediate. Deprotection of the THP and N6-benzoyl groups is accomplished using standard methodologies and standard methods may be used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine is accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies may be used to obtain the 5'-DMT- and 5'-DMT-3'-phosphoramidites.

2'-Fluorouridine

Synthesis of 2'-deoxy-2'-fluorouridine is accomplished by the modification of a literature procedure in which 2,2'-anhydro-1-beta-D-arabinofuranosyluracil is treated with 70% hydrogen fluoride-pyridine. Standard procedures may be used to obtain the 5'-DMT and 5'-DMT-3' phosphoramidites.

2'-Fluorodeoxycytidine

2'-deoxy-2'-fluorocytidine is synthesized via amination of 2'-deoxy-2'-fluorouridine, followed by selective protection to give N4-benzoyl-2'-deoxy-2'-fluorocytidine. Standard procedures may be used to obtain the 5'-DMT and 5'-DMT3' phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta,* 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) are added to DMF (300 mL). The mixture is heated to reflux, with stirring, allowing the evolved carbon dioxide gas to be released in a controlled manner. After 1 hour, the slightly darkened solution is concentrated under reduced pressure. The resulting syrup is poured into diethylether (2.5 L), with stirring. The product formed a gum. The ether is decanted and the residue is dissolved in a minimum amount of methanol (ca. 400 mL). The solution is poured into fresh ether (2.5 L) to yield a stiff gum. The ether is decanted and the gum is dried in a vacuum oven (60° C. at 1 mm Hg for 24 h) to give a solid that is crushed to a light tan powder (57 g, 85% crude yield). The NMR spectrum is consistent with the structure, contaminated with phenol as its sodium salt (ca. 5%). The material is used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) may be added to a 2 L stainless steel pressure vessel and placed in a pre-heated oil bath at 160° C. After heating for 48 hours at 155–160° C., the vessel is opened and the solution evaporated to dryness and triturated with MeOH (200 mL). The residue is suspended in hot acetone (1 L). The insoluble salts may be filtered, washed with acetone (150 mL) and the filtrate evaporated. The residue (280 g) is dissolved in $CH_3CN$ (600 mL) and evaporated. A silica gel column (3 kg) is packed in $CH_2Cl_2$/acetone/MeOH (20:5:3) containing 0.5% $Et_3NH$. The residue is dissolved in $CH_2Cl_2$ (250 mL) and adsorbed onto silica (150 g) prior to loading onto the column. The product is eluted with the packing solvent to give 160 g (63%) of product. Additional material is obtained by reworking impure fractions.

2'-O-Methoxyethyl-5'-O-dimethoxytrityl-5-methyluridine

2'-O-Methoxyethyl-5-methyluridine (160 g, 0.506 M) is co-evaporated with pyridine (250 mL) and the dried residue dissolved in pyridine (1.3 L). A first aliquot of dimethoxytrityl chloride (94.3 g, 0.278 M) is added and the mixture stirred at room temperature for one hour. A second aliquot of dimethoxytrityl chloride (94.3 g, 0.278 M) is added and the reaction stirred for an additional one hour. Methanol (170 mL) is then added to stop the reaction. HPLC showed the presence of approximately 70% product. The solvent is evaporated and triturated with $CH_3CN$ (200 mL). The residue is dissolved in $CHCl_3$ (1.5 L) and extracted with 2×500 mL of saturated $NaHCO_3$ and 2×500 mL of saturated NaCl. The organic phase is dried over $Na_2SO_4$, filtered and evaporated. 275 g of residue is obtained. The residue is purified on a 3.5 kg silica gel column, packed and eluted with EtOAc/hexane/acetone (5:5:1) containing 0.5% $Et_3NH$. The pure fractions may be evaporated to give 164 g of product. Approximately 20 g additional is obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) may be combined and stirred at room temperature for 24 hours. The reaction is monitored by TLC by first quenching the TLC sample with the addition of MeOH. Upon completion of the reaction, as judged by TLC, MeOH (50 mL) is added and the mmixture evaporated at 35° C. The residue is dissolved in $CHCl_3$ (800 mL) and extracted with 2×200 mL of saturated sodium bicarbonate and 2×200 mL of saturated NaCl. The water layers may be back extracted with 200 mL of $CHCl_3$. The combined organics may be dried with sodium sulfate and evaporated to give 122 g of residue (approx. 90% product). The residue is purified on a 3.5 kg silica gel column and eluted using EtOAc/hexane (4:1). Pure product fractions may be evaporated to yield 96 g (84%). An additional 1.5 g is recovered from later fractions.

3'-O-Acetyl-2'-O-methoxyethyl-5'-O-dimethoxytrityl-5-methyl-4-triazoleuridine

A first solution is prepared by dissolving 3'-O-acetyl2'-O-methoxyethyl-5'-O-dimethoxytrityl-5-methyluridine (96 g, 0.144 M) in $CH_3CN$ (700 mL) and set aside. Triethylamine (189 mL, 1.44 M) is added to a solution of triazole (90 g, 1.3 M) in $CH_3CN$ (1 L), cooled to −5° C. and stirred for 0.5 h using an overhead stirrer. $POCl_3$ is added dropwise, over a 30 minute period, to the stirred solution maintained at 0–10° C., and the resulting mixture stirred for an additional 2 hours. The first solution is added dropwise, over a 45 minute period, to the latter solution. The resulting reaction mixture is stored overnight in a cold room. Salts may be filtered from the reaction mixture and the solution is evaporated. The residue is dissolved in EtOAc (1 L) and the insoluble solids may be removed by filtration. The filtrate is ished with 1×300 mL of $NaHCO_3$ and 2×300 mL of saturated NaCl, dried over sodium sulfate and evaporated. The residue is triturated with EtOAc to give the title compound.

2'-O-Methoxyethyl-5'-O-dimethoxytrityl-5-methylcytidine

A solution of 3'-O-acetyl-2'-O-methoxyethyl-5'-Odimethoxytrityl-5-methyl-4-triazoleuridine (103 g, 0.141 M) in dioxane (500 mL) and $NH_4OH$ (30 mL) is stirred at room temperature for 2 hours. The dioxane solution is evaporated and the residue azeotroped with MeOH (2×200 mL). The residue is dissolved in MeOH (300 mL) and transferred to a 2 liter stainless steel pressure vessel. MeOH (400 mL) saturated with NH$_3$ gas is added and the vessel heated to 100° C. for 2 hours (TLC showed complete conversion). The vessel contents may be evaporated to dryness and the residue is dissolved in EtOAc (500 mL) and washed once with saturated NaCl (200 mL). The organics may be dried over sodium sulfate and the solvent is evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) is dissolved in DMF (800 mL) and benzoic anhydride (37.2 g, 0.165 M) is added with stirring. After stirring for 3 hours, TLC showed the reaction to be approximately 95% complete. The solvent is evaporated and the residue azeotroped with MeOH (200 mL). The residue is dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue is chromatographed on a 1.5 kg silica column using EtOAc/hexane (1:1) containing 0.5% Et$_3$NH as the eluting solvent. The pure product fractions may be evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) is dissolved in CH$_2$Cl$_2$ (1 L) Tetrazole diisopropylamine (7.1 g) and 2-cyanoethoxy-tetra-(isopropyl) phosphite (40.5 mL, 0.123 M) may be added with stirring, under a nitrogen atmosphere. The resulting mixture is stirred for 20 hours at room temperature (TLC showed the reaction to be 95% complete). The reaction mixture is extracted with saturated NaHCO$_3$ (1×300 mL) and saturated NaCl (3×300 mL). The aqueous washes may be back-extracted with CH$_2$Cl$_2$ (300 mL), and the extracts may be combined, dried over MgSO$_4$ and concentrated. The residue obtained is chromatographed on a 1.5 kg silica column using EtOAc/hexane (3:1) as the eluting solvent. The pure fractions may be combined to give 90.6 g (87%) of the title compound. 2'-O-(Aminooxyethyl) nucleoside amidites and 2'-O-(dimethylaminooxyethyl) nucleoside amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) may be dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) is added in one portion. The reaction is stirred for 16 h at ambient temperature. TLC (Rf 0.22, ethyl acetate) indicated a complete reaction. The solution is concentrated under reduced pressure to a thick oil. This is partitioned between dichloromethane (1 L) and saturated sodium bicarbonate (2×1 L) and brine (1 L). The organic layer is dried over sodium sulfate and concentrated under reduced pressure to a thick oil. The oil is dissolved in a 1:1 mixture of ethyl acetate and ethyl ether (600 mL) and the solution is cooled to −10° C. The resulting crystalline product is collected by filtration, washed with ethyl ether (3×200 mL) and dried (40° C, 1 mm Hg, 24 h) to 149 g (74.8%) of white solid. TLC and NMR may be consistent with pure product.

5'-O-tert-Butyldiphenylsilyl-2'-O-(2-hydroxyethyl)-5-methyluridine

In a 2 L stainless steel, unstirred pressure reactor is added borane in tetrahydrofuran (1.0 M, 2.0 eq, 622 mL). In the fume hood and with manual stirring, ethylene glycol (350 mL, excess) is added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) may be added with manual stirring. The reactor is sealed and heated in an oil bath until an internal temperature of 160° C. is reached and then maintained for 16 h (pressure<100 psig). The reaction vessel is cooled to ambient and opened. TLC (Rf 0.67 for desired product and Rf 0.82 for ara-T side product, ethyl acetate) indicated about 70% conversion to the product. In order to avoid additional side product formation, the reaction is stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue is purified by column chromatography (2 kg silica gel, ethyl acetate-hexanes gradient 1:1 to 4:1). The appropriate fractions may be combined, stripped and dried to product as a white crisp foam (84 g, 50%), contaminated starting material (17.4 g) and pure reusable starting material 20 g. The yield based on starting material less pure recovered starting material is 58%. TLC and NMR may be consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) is mixed with triphenylphosphine (11.63 g, 44.36 mmol) and N-hydroxyphthalimide (7.24 g, 44.36 mmol). It is then dried over P$_2$O$_5$ under high vacuum for two days at 40° C. The reaction mixture is flushed with argon and dry THF (369.8 mL, Aldrich, sure seal bottle) is added to get a clear solution. Diethylazodicarboxylate (6.98 mL, 44.36 mmol) is added dropwise to the reaction mixture. The rate of addition is maintained such that resulting deep red coloration is just discharged before adding the next drop. After the addition is complete, the reaction is stirred for 4 hrs. By that time TLC showed the completion of the reaction (ethylacetate:hexane, 60:40). The solvent is evaporated in vacuum. Residue obtained is placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) is dissolved in dry CH$_2$Cl$_2$ (4.5 mL) and methylhydrazine (300 mL, 4.64 mmol) is added dropwise at −10° C. to 0° C. After 1 h the mixture is filtered, the filtrate is washed with ice cold CH$_2$Cl$_2$ and the combined organic phase is washed with water, brine and dried over anhydrous Na$_2$SO$_4$. The solution is concentrated to get 2'-O-(aminooxyethyl) thymidine, which is then dissolved in MeOH (67.5 mL). To this formaldehyde (20% aqueous solution, w/w, 1.1 eq.) is added and the resulting mixture is stirred for 1 h. Solvent is removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy)ethyl]-5-methyluridine (1.77 g, 3.12 mmol) is dissolved in a solution of 1M pyridinium p-toluenesulfonate (PPTS) in dry MeOH (30.6 mL). Sodium cyanoborohydride (0.39 g, 6.13 mmol) is added to this solution at 10° C. under inert atmosphere. The reaction mixture is stirred for 10 minutes at 10° C. After that the reaction vessel is removed from the ice bath and stirred at room temperature for 2 h, the reaction monitored by TLC (5% MeOH in $CH_2Cl_2$). Aqueous $NaHCO_3$ solution (5%, 10 mL) is added and extracted with ethyl acetate (2×20 mL). Ethyl acetate phase is dried over anhydrous $Na_2SO_4$, evaporated to dryness. Residue is dissolved in a solution of 1M PPTS in MeOH (30.6 mL). Formaldehyde (20% w/w, 30 mL, 3.37 mmol) is added and the reaction mixture is stirred at room temperature for 10 minutes. Reaction mixture cooled to 10° C. in an ice bath, sodium cyanoborohydride (0.39 g, 6.13 mmol) is added and reaction mixture stirred at 10° C. for 10 minutes. After 10 minutes, the reaction mixture is removed from the ice bath and stirred at room temperature for 2 hrs. To the reaction mixture 5% $NaHCO_3$ (25 mL) solution is added and extracted with ethyl acetate (2×25 mL). Ethyl acetate layer is dried over anhydrous $Na_2SO_4$ and evaporated to dryness. The residue obtained is purified by flash column chromatography and eluted with 5% MeOH in $CH_2Cl_2$ to get 5-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) is dissolved in dry THF and triethylamine (1.67 mL, 12 mmol, dry, kept over KOH). This mixture of triethylamine-2 HF is then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction is monitored by TLC (5% MeOH in $CH_2Cl_2$). Solvent is removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) is dried over $P_2O_5$ under high vacuum overnight at 40° C. It is then co-evaporated with anhydrous pyridine (20 mL). The residue obtained is dissolved in pyridine (11 mL) under argon atmosphere. 4-dimethylaminopyridine (26.5 mg, 2.60 mmol), 4,4'-dimethoxytrityl chloride (880 mg, 2.60 mmol) is added to the mixture and the reaction mixture is stirred at room temperature until all of the starting material disappeared. Pyridine is removed under vacuum and the residue chromatographed and eluted with 10% MeOH in $CH_2Cl_2$ (containing a few drops of pyridine) to get 5'-O-DMT-2'-O-(dimethylaminooxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) is co-evaporated with toluene (20 mL). To the residue N,N-diisopropylamine tetrazonide (0.29 g, 1.67 mmol) is added and dried over $P_2O_5$ under high vacuum overnight at 40° C. Then the reaction mixture is dissolved in anhydrous acetonitrile (8.4 mL) and 2-cyanoethyl-N,N,$N^1$,$N^2$-tetraisopropylphosphoramidite (2.12 mL, 6.08 mmol) is added. The reaction mixture is stirred at ambient temperature for 4 hrs under inert atmosphere. The progress of the reaction is monitored by TLC (hexane:ethyl acetate 1:1). The solvent is evaporated, then the residue is dissolved in ethyl acetate (70 mL) and washed with 5% aqueous $NaHCO_3$ (40 mL). Ethyl acetate layer is dried over anhydrous $Na_2SO_4$ and concentrated. Residue obtained is chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites 2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly. N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl)diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,40 -dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—N$(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O2-,2'-anhydro-5-methyluridine (1.2 g, 5 mmol), and sodium bicarbonate (2.5 mg) are added and the bomb is sealed, placed in an oil bath and heated to 155 C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2 (2-N,N-dimethylaminoethoxy)ethyl)]-5-methyl Uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with CH2Cl2 (2×200 mL). The combined CH2Cl2 layers are washed with saturated NaHCO3 solution, followed by saturated NaCl solution and dried over anhydrous sodium sulfate. Evaporation of the solvent followed by silica gel chromatography using MeOH:CH2Cl2:Et3N (20:1, v/v, with 1% triethylamine) gives the title compound.

5'-O-Dimethoxytrityl-2'-O-[2(2-N,N-dimethylaminoethoxy)ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in CH2Cl2 (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle is replaced by 0.2 M solution of 3H-1,2-benzodithiole-3-one 1,1-dioxide in acetonitrile for the stepwise thiation of the phosphite linkages. The thiation wait step is increased to 68 sec and is followed by the capping step. After cleavage from the CPG column and deblocking in concentrated ammonium hydroxide at 55° C. (18 h), the oligonucleotides may be purified by precipitating twice with 2.5 volumes of ethanol from a 0.5 M NaCl solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. , 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

Synthesis of Chimeric Oligonucleotides

Chimeric oligonucleotides, oligonucleosides or mixed oligonucleotides/oligonucleosides can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O—Me]--[2'-O-deoxy]--[2'-O—Me] Chimeric Phosphorothioate Oligonucleotides

Chimeric oligonucleotides having 2'-O-alkyl phosphorothioate and 2'-O-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample is again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]--[2'-deoxy]--[2'-O-(Methoxyethyl)] Chimeric Phosphorothioate Oligonucleotides

[2'-O-(2-methoxyethyl)]--[2'-deoxy]--[-2'-O-(methoxyethyl)] chimeric phosphorothioate oligonucleotides may be prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]--[2'-deoxy Phosphorothioate]--[2'-O-(2-Methoxyethyl) Phosphodiester] Chimeric Oligonucleotides

[2'-O-(2-methoxyethyl phosphodiester]--[2'-deoxy phosphorothioate]--[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides may be analyzed by polyacrylamide gel electrophoresis on denaturing gels and judged to be at least 85% full length material. The relative amounts of phosphorothioate and phosphodiester linkages obtained in synthesis may be periodically checked by $^{31}$P nuclear magnetic resonance spectroscopy, and for some studies oligonucleotides may be purified by HPLC, as described by Chiang et al., J. Biol. Chem. 1991, 266, 18162–18171. Results obtained with HPLC-purified material may be similar to those obtained with non-HPLC purified material.

Example 6

Alternative Pathway Reconstitution

The alternative pathway was reconstituted with purified human proteins essentially as described by Keil (Keil et al., *Am J Hematol* 1995;50(4):254–62).

Example 7

Complement Activity Assay

Measurement of complement activity was accomplished by measuring C3 convertase activity by combining the following C3 (125 µg/ml), Factor B (20 µg/ml) and Factor D (0.2 µg/ml) in Hand's Balanced Salt Solution (HBSS) buffered with 5 mM HEPES, pH 7.2. Incubations may be carried out under ambient conditions in the presence of oligonucleotide (concentrations up to 300 µg/ml). Aliquots may be removed at selected intervals and immediately diluted 50-fold in ice cold ELISA dilution buffer. Complement split products may be measured by ELISA.

In another example measurement of complement activity was accomplished by measuring C3 convertase activity by combining the following C3 (125 µg/ml), Factor B (20 µg/ml) Factor D (0.2 µg/ml), Factor H (25 µg/ml) and Factor I (2 µg/ml) in Hand's Balanced salt Solution (HBSS) buffered with 5 mM HEPES, pH 7.2. Incubations were carried out under ambient conditions in the presence of oligonucleotide concentrations (up to 300 µg/ml). Aliquots were removed at selected intervals and immediately diluted 50-fold in ice cold ELISA dilution buffer. Complement split products were measured by ELISA. Complement activation in serum was measured in both rhesus monkey and human serum as follows:

Dilutions of oligonucleotides were added to normal human or rhesus serum at a 1:10–1:20 ratio, v/v. The samples were incubated at 37° C. and aliquots removed at selected intervals. Complement activation was terminated by either placing the aliquots in an acid precipitating reagent for RIA determinations, or by diluting the aliquots 1:50 in ice cold sample diluent for ELISA determinations.

As controls for some experiments zymosan A (500 µg/ml) or cobra venom factor (CVF; 2 U/ml) were used to activate the alternative pathway in the presence of the oligonucleotide. Each was added at a final volume of 1:20.

Example 8

In vivo Activation of Complement

Cynomolgus monkeys received single doses of 2 to 20 mg/kg of oligonucleotide or a vehicle control solution by i.v. infusion for periods ranging from 2 to 120 minutes. Measurement:

The level of complement split products Bb, C3a, C4a and C5a was determined in EDTA plasma samples using commercially available (Amersham Life Sciences, Amersham, Little Chalfont, Buckinghamshire, England; Quidel, San Diego, Calif.) radioimmunoassay or enzyme-linked immunosorbent assay kits.

Total hemolytic complement activity in serum (CH50) was assayed in serum samples using the standard hemolytic assay (Harbeck et al., *Diagnostic Immunology Laboratory Manual.* pp 9–20, Raven Press, New York, 1991). Factor H concentrations in monkey plasma was determined by radial immunodiffusion (Harbeck et al.) using an anti-human Factor H antibody.

What is claimed is:

1. A method for modulating complement activation in a cell, tissue or a bodily fluid comprising independently administering to said cell, tissue or bodily fluid a first concentration and a second, independent concentration of an oligonucleotide which comprises one or more phosphorothioate modifications, wherein said oligonucleotide initiates complement activation at said first concentration and inhibits complement activation at said second, independent concentration.

2. The method of claim 1, wherein said first concentration is less than or equal to 80 µg/ml.

3. The method of claim 1, wherein said second concentration is at least 200 µg/ml.

* * * * *

UNITED STATES PATENT AND TRADEMARK OFFICE
CERTIFICATE OF CORRECTION

PATENT NO. : 6,232,296 B1  
DATED : May 15, 2001  
INVENTOR(S) : Henry

It is certified that error appears in the above-identified patent and that said Letters Patent is hereby corrected as shown below:

Column 1,
Line 55, please delete "various" and insert -- Various --.

Column 10,
Line 54, please delete "methylimino)" and insert -- (methylimino) --.

Column 21,
Line 30, Example 1, please delete "DMT3'" and insert -- DMT-3' --.

Column 22,
Line 34, Example 1, please delete "mmixture" and insert -- mixture --.
Line 63, Example 1, please delete "Odimethoxytrityl" and insert -- O-dimethoxytrityl --.

Column 25,
Line 57, Example 1, please delete "N, N, $N^1$, $N^2$" and insert -- N, N, $N^1$, $N^1$ --.

Column 26,
Line 28, Example 1, please delete "5-O-(4, 40" and insert -- 5-O- (4, 4 --.

Column 28,
Line 25, Example 4, please delete "[2 ' -0-deoxy]" and insert -- [2 ' -deoxy] --.
Line 28, Example 4, please delete "2 ' -0-deoxy" and insert -- 2 ' -deoxy --.

Signed and Sealed this

Sixth Day of August, 2002

*Attest:*

JAMES E. ROGAN  
*Director of the United States Patent and Trademark Office*

*Attesting Officer*

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 1
gcccaagctg gcatccgtca                                              20
```